(12) United States Patent
Giering et al.

(10) Patent No.: US 9,878,573 B2
(45) Date of Patent: Jan. 30, 2018

(54) AUTHENTICITY FEATURE IN THE FORM OF LUMINESCENT SUBSTANCES

(75) Inventors: Thomas Giering, Kirchseeon (DE); Peter Kersten, Feldkirchen Westerham (DE); Ulrich Magg, Dachau (DE); Gregor Grauvogl, Oberhaching (DE)

(73) Assignee: GIESECKE+DEVRIENT CURRENCY TECHNOLOGY GMBH, Munich (DE)

( * ) Notice: Subject to any disclaimer, the term of this patent is extended or adjusted under 35 U.S.C. 154(b) by 34 days.

(21) Appl. No.: 13/515,317

(22) PCT Filed: Dec. 15, 2010

(86) PCT No.: PCT/EP2010/007689
§ 371 (c)(1),
(2), (4) Date: Jun. 12, 2012

(87) PCT Pub. No.: WO2011/082794
PCT Pub. Date: Jul. 14, 2011

(65) Prior Publication Data
US 2012/0256409 A1    Oct. 11, 2012

(30) Foreign Application Priority Data
Dec. 16, 2009 (DE) .................. 10 2009 058 669

(51) Int. Cl.
*B42D 25/378* (2014.01)
*C09K 11/71* (2006.01)
(Continued)

(52) U.S. Cl.
CPC ........... *B42D 25/378* (2014.10); *B42D 25/21* (2014.10); *B42D 25/29* (2014.10); *B42D 25/36* (2014.10);
(Continued)

(58) Field of Classification Search
CPC ........... B42D 15/00; B42D 15/10; G09C 3/00
(Continued)

(56) References Cited

U.S. PATENT DOCUMENTS

| 4,451,530 A | 5/1984 | Kaule et al. |
| 4,463,970 A | 8/1984 | Kaule et al. |

(Continued)

FOREIGN PATENT DOCUMENTS

| DE | 3048734 A1 | 7/1982 |
| FR | 2554122 A1 | 3/1985 |

(Continued)

OTHER PUBLICATIONS

International Search Report and Written Opinion, dated May 23, 2011.

*Primary Examiner* — Justin V Lewis
(74) *Attorney, Agent, or Firm* — Justin Cassell; Workman Nydegger

(57) ABSTRACT

The invention relates to a security element having at least two luminescent substances. The invention starts out from a security element having at least two luminescent substances, whereby the security element has a first and a second luminescent substance which have a substantially identical, joint emission band, whereby at least the first or the second luminescent substance, or both luminescent substances, have at least one excitation band that leads to an emission at the joint emission band only in the case of the first or the second luminescent substance.

27 Claims, 1 Drawing Sheet

(51) Int. Cl.

| | | |
|---|---|---|
| *C09K 11/77* | (2006.01) | |
| *G07D 7/12* | (2016.01) | |
| *B42D 25/29* | (2014.01) | |
| *B42D 25/21* | (2014.01) | |
| *B42D 25/36* | (2014.01) | |
| *G01N 21/01* | (2006.01) | |
| *G01N 21/64* | (2006.01) | |
| *G07D 7/1205* | (2016.01) | |
| *B42D 25/382* | (2014.01) | |
| *B42D 25/387* | (2014.01) | |

(52) U.S. Cl.
CPC ......... *C09K 11/71* (2013.01); *C09K 11/7771* (2013.01); *C09K 11/7776* (2013.01); *G01N 21/01* (2013.01); *G01N 21/6447* (2013.01); *G07D 7/12* (2013.01); *G07D 7/1205* (2017.05); *B42D 25/382* (2014.10); *B42D 25/387* (2014.10); *B42D 2035/34* (2013.01); *G01N 2201/06113* (2013.01)

(58) Field of Classification Search
USPC ...... 283/67, 70, 72, 87, 91, 92, 94, 95, 901, 283/902
See application file for complete search history.

(56) References Cited

U.S. PATENT DOCUMENTS

| | | |
|---|---|---|
| 6,344,261 B1 | 2/2002 | Kaule et al. |
| 6,479,133 B1 | 11/2002 | Kaule et al. |
| 6,506,476 B1 | 1/2003 | Kaule et al. |
| 7,927,511 B2 | 4/2011 | Giering et al. |
| 2004/0027652 A1* | 2/2004 | Erdogan et al. ............ 359/359 |
| 2007/0202352 A1 | 8/2007 | Giering et al. |
| 2008/0116272 A1* | 5/2008 | Giering .................. G07D 7/122 235/439 |

FOREIGN PATENT DOCUMENTS

| | | | |
|---|---|---|---|
| WO | | 8103508 A1 | 12/1981 |
| WO | | 9939051 A1 | 1/1999 |
| WO | | 9938700 A1 | 8/1999 |
| WO | | 9938701 A1 | 8/1999 |
| WO | | 2005035271 A2 | 4/2005 |
| WO | | 2006024530 A1 | 3/2006 |
| WO | WO | 2006024530 A1 * | 3/2006 |
| WO | | 2009136921 A1 | 11/2009 |

* cited by examiner

AUTHENTICITY FEATURE IN THE FORM OF LUMINESCENT SUBSTANCES

BACKGROUND OF THE INVENTION

A. Field of the Invention

This invention relates to a security element having at least two luminescent substances.

B. Related Art

The designation "value document" is to be understood within the framework of the invention to refer to bank notes, checks, shares, tokens, identity cards, credit cards, passports and also other documents as well as labels, seals, packages or other elements for product authentication.

The safeguarding of value documents against forgery by means of luminescent substances has been known for some time. The employment of transition metals and rare earth metals as luminescent ions in host lattices has already been discussed. Such ions have the advantage that, after suitable excitation, they show one or several characteristic narrow-band luminescences which facilitate a reliable detection and the delimitation over other spectra. Combinations of transition metals and/or rare earth metals have also been discussed. Such substances have the advantage that, in addition to the above-mentioned luminescences, there are observed so-called energy transfer processes which can lead to complicated spectra. In such energy transfer processes an ion can transfer its energy to another ion, and the spectra can then consist of several narrow-band lines which are characteristic of both ions.

Ions with characteristic properties which are suited for safeguarding value documents are limited in number, however. Moreover, ions of the transition metals and/or rare earth metals luminesce at one or several characteristic wavelengths which are dependent on the nature of the ion and of the host lattice and can be predicted. Energy transfer processes also lead to these characteristic luminescences of the involved ions.

With all known security elements and the luminescent substances employed for the security elements, however, a detection of the security elements or of the contained luminescent substances is done by exploiting the fact that their emissions, i.e. their characteristic luminescences, are distinguishable. In particular, the emissions have different wavelengths, so that they can be uniquely identified via the respective emission wavelength. Other criteria may be for example the decay time of the emission or its intensity. Such security elements are known for example from the documents WO 2009/136921 A1, WO 2006/024530 A1, WO 2005/035271 A2, WO 81/03508 A1, WO 99/38700 A1, WO 99/38701 A1, WO 99/39051 A1 and DE 30 48 734 A1.

The described security elements for safeguarding value documents consist of individual luminophores which differ with regard to their spectral and/or temporal properties. The security elements are applied into and/or onto value documents in different forms of use. In so doing, a combination of luminophores can be employed. The emission bands of the employed luminophores represent a spectral encoding. Several different luminophores can be combined to systems, whereby the individual systems are mutually independent. The emission of the employed luminophores is also referred to as luminescence, which may involve fluorescence and/or phosphorescence.

The above-mentioned limited number of luminophores, the limited number of different spectral lines emitted thereby, makes it necessary, for a discrimination of the different luminophores, to mutually coordinate the emissions of the employed luminophores such that the emissions of the different luminescences for a value document do not overlap. Thus there are only very limited possibilities for integrating different luminophores in an individual value document such that the value document can be reliably distinguished from other value documents.

Starting out from this prior art, the invention is based on the object of stating security elements having at least two luminescent substances which are suited in particular as an authenticity marking for value documents, whereby the security elements are to offer an even higher security against attempts at forgery. Moreover, there is to be obtained an increase in the variety of distinguishable security elements.

The invention starts out from a security element having at least two luminescent substances, whereby the security element has a first and a second luminescent substance which have a substantially identical, joint emission band, whereby at least the first or the second luminescent substance, or both luminescent substances, have at least one excitation band that leads to an emission at the joint emission band only in the case of the first or the second luminescent substance.

The invention has the advantage that it is now also possible to use for safeguarding a value document luminescent substances together that could previously not be distinguished, or not distinguished reliably, by their emissions. The different excitation bands permit a distinction of the luminescent substances while the emission band is the same. Thus, the available possibilities for safeguarding value documents are substantially increased. This allows the provision of a multiplicity of additional encodings. Moreover, the fact that the luminescent substances cannot be distinguished solely by their emissions substantially improves the safeguarding effected by the security element containing the luminescent substances.

Especially advantageously, the security element can be used for safeguarding and/or encoding value documents. For example, by incorporation and/or application to the value document or by incorporation or application to authentication features for value documents.

A verification of the presence of a security element, of a value document or of an authentication feature can be effected by exciting the luminescent substances with a first radiation which has a wavelength lying substantially at one of the excitation bands that leads to an emission at the joint emission band only in the case of the first or the second luminescent substance.

This verification by excitation at different wavelengths that correspond to the different excitation bands of the jointly employed luminescent substances allows one to also be able to mutually distinguish luminescent substances that were hitherto perceived as a single luminescent substance, because they have a joint emission band.

DESCRIPTION OF THE DRAWINGS

Further advantages of the present invention can be found in the dependent claims as well as the subsequent description of embodiments with reference to figures.

There are shown.

DETAILED DESCRIPTION OF EXEMPLARY EMBODIMENTS

Figure 1A:
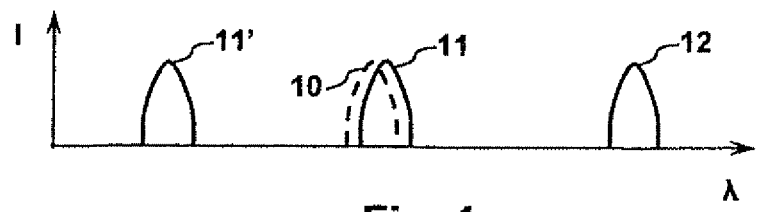
FIGS. 1a-1b show excitation bands and emission bands of security elements.

FIG. 1 shows excitation bands and emission bands of security elements that are employed for example for safeguarding value documents. The security elements consist of a specific combination of luminescent substances. For the security element there are employed at least two different luminescent substances, hereinafter also referred to as luminophores, for one value document, e.g. jointly incorporated onto or into the value document, in particular in the substrate (paper and/or plastic) by means of planchets, fibers, etc. The luminophores are so incorporated or applied that they overlap spatially at least in parts, preferably are both present jointly wherever they are present, in order that the luminophores appear as a joint luminophore upon an attempt at metrological analysis. Further luminophores can be present. If further luminophores are present, there will hereinafter be spoken of at least two luminescence systems, rather than of at least two different luminescent substances or luminophores.

The at least two luminescence systems are selected such that they possess at least one joint emission, i.e. emit at at least one joint wavelength upon (possibly different) excitation. By "joint wavelength/joint emission" it is to be understood here that there occurs a spectral overlap of the emission spectra of the at least one joint emission or at least a very near emission (e.g. directly adjacent), so that the emissions appear as a joint emission, i.e. cannot be mutually discriminated significantly, using sensors with a resolution of >50 nm, in particular >10 nm.

Further, the "joint emission" can have an approximately identical line width for both luminophores, whereby the at least two luminescence systems possess at least one wavelength at which they are not jointly excitable, i.e. either only one of the two luminescence systems is excitable (while at the other wavelengths at which the luminescence systems are excitable, both luminescence systems are excitable), or there is for both luminescence systems at least one wavelength, respectively, at which only the one respective luminescence system is excitable, while the other is not or with much lower efficiency. By "lower efficiency" there is to be understood here a factor of less than 5, preferably less than 10. The at least one wavelength in the joint emission produces, upon excitation of similar intensity, likewise similar intensity which is comparable to that of the joint or other excitation. Similar intensity means here that in the excitation spectrum of the joint emission the heights of the two excitation bands differ no more than by a factor of 10, preferably no more than by a factor of 5, particularly preferably no more than by a factor of 3, very particularly preferably no more than by a factor of 2, even much more preferably no more than by a factor of 1.07.

The invention exploits energy transfer systems in which energy is transferred from a sensitizer (optical receiver) to a luminophore. This can be effected completely or also only partly. The invention utilizes the surprising finding that with suitable detection methods it is also possible to utilize systems that could hitherto not be discriminated, and were therefore not usable, because of interactions of the emissions.

When the systems are excited unselectively, there is obtained upon excitation with the excitation wavelengths of the first luminophore as well as upon the excitation with the excitation wavelengths of the second luminophore a (the) joint luminescence emission (although out of the two different systems). However, when excitation is done at the at least one (preferably the two different individual) wavelengths at which only the one luminophore is respectively excitable, there is obtained the emission from only one of the two systems in isolation.

In FIG. 1a there are represented intensities as a function of wavelength for a first luminophore which has a first excitation band 11 and a second excitation band 11' for the emission band 12. A second luminophore has only one excitation band 10, likewise for the emission band 12, which is almost identical to the excitation band 11 of the first luminophore. Upon an excitation with a radiation with a wavelength that corresponds to the excitation bands 10, 11, the first and second luminophores can thus not be distinguished. The excitation with a radiation at the second excitation band 11', however, makes it possible to discriminate the first luminophore from the second luminophore.

Figure 1B:
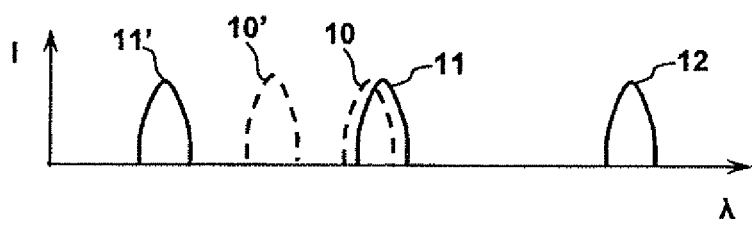

In FIG. 1b there are represented intensities as a function of wavelength for a first luminophore which has a first excitation band 11 and a second excitation band 11' for the emission band 12. A second luminophore has only one excitation band 10, likewise for the emission band 12, which is almost identical to the excitation band 11 of the first luminophore. Additionally, the second luminophore has a second excitation band 10' for the emission band 12. Upon an excitation with a radiation with a wavelength that corresponds to the excitation bands 10, 11, the first and second luminophores can thus not be distinguished. The excitation with a radiation at the second excitation band 11' of the first luminophore, however, makes it possible to recognize the first luminophore. The excitation with a radiation at the second excitation band 10' of the second luminophore, however, makes it possible to recognize the second luminophore.

The wavelengths stated in the subsequent examples are stated approximately. The actual values are determined by the employed matrix or the employed host lattice.

Example 1

Luminescence System 1: Er:Matrix
Luminescence System 2: Yb,Tm:Matrix

Both luminescence systems emit at 1 μm upon excitation with visible or NIR wavelengths and can thus not be discriminated via the emission at 1 μm. They can of course be discriminated at other wavelengths, but there then remains the uncertainty of the intensity in the joint line. Therefore, the evaluating of the joint line is decisive for the invention.

Er:matrix possesses excitation at 520 nm, 650 nm and 800 nm

Yb,Tm:matrix possesses joint excitation at 800 nm, but the system can likewise be excited at 700 nm, at which the system 1 possesses no excitation.

When the feature system (i.e. the combination of luminescence system 1 and luminescence system 2) is incorporated into the volume of the bank note (or into an ink), the system respectively shows an emission at 1 μm upon all excitations 520, 650, 700 nm. When the system is excited at 800 nm, there is likewise observed an emission at 1 μm, but it arises in this case out of both luminescence systems.

Example 2

Luminescence System 1: Tm:Matrix
Luminescence System 2: Yb,Tm:Matrix

Both luminescence systems emit at 1.9 μm. Systems 1 and 2 are excitable wherever Tm is excitable, e.g. at 800 nm. However, the system 2 is additionally excitable at approx. 980 nm.

When the feature system (i.e. the combination of luminescence system 1 and luminescence system 2) is incorporated into a joint ink, they emit upon excitation into all Tm bands out of both systems. Only upon excitation at approx. 980 nm is the luminescence system 2 exclusively excited.

Particularly preferable are feature systems if they have only one emission (or only one substantial emission).

For the invention all luminophores are suitable in principle. Particularly preferable are luminophores with a greater number of narrow-band emission bands and/or excitation bands. Particularly preferable rare earth systems, i.e. host lattices doped with rare earth ions as luminophores, with their narrow-band numerous lines. Hereinafter these systems will be referred to as luminophore:matrix, whereby the luminophore is doped into the matrix or into the host lattice.

Particularly preferably, Stokes-shifted systems are employed, because they are available with high efficiency, i.e. can be low doped.

The following Table 1 gives an overview of possible systems according to the invention with emissions in the IR region. The principle can likewise be applied to luminophores with emissions in the visible spectral range.

TABLE 1

| One luminophore | One or several luminophores |
|---|---|
| A, AB, ABC, AC, ACD, AED | AD |
| C, BC, CDE | CD, BCD |
| F, BF, CF, DF, DEF, BDF | |
| E, BE, DE, GE, CGE | |
| A, AB, AG | |
| E, IE, EGH | |
| AD, GI, EGJ | D, ED, GH |
| E, EI | |
| C, CJ, CH, FH | KH |

In Table 1 the letters A to K stand for sets of luminophores. The luminophores contained in the sets A to K are stated hereinafter:

| | | |
|---|---|---|
| A = {Ho} | B ∈ {Cr, Fe, Mn} | C = {Tm} |
| D ∈ {Yb, Er} | E = {Nd} | F = {Er} |
| G = {Yb} | H ∈ {Er, Tm} | I ∈ {Yb, Cr} |
| J ∈ {Ho, Tm} | K ∈ {Cr} | |

A luminescence system results from the selection of one or several of the luminophores.

For the feature system of the invention there are used two (or also several) of the luminescence systems. The two luminescence systems can either be individual luminophores, or themselves again mixtures of luminophores. Particularly preferably, the luminescence systems have luminophores of a group with an identical emission wavelength. Such groups of different luminophores with identical emission wavelengths are respectively put together in a line of Table 1.

The luminophores are inserted into suitable host lattices. Particularly preferable are inorganic host lattices, in particular because of the narrow-band nature of the spectral lines determining the luminescence.

The role of the matrix is not decisive for the present invention. However, it can be employed for fine-tuning the excitation bands or emission bands. This is relevant in particular when excitation is done with narrow-band excitation sources (e.g. lasers). Then there can also be employed according to the invention RE:matrix A and (identical) RE:matrix B.

Preferred are matrices from the family of the garnets, perovskites, sulfides, oxysulfides, apatites, vanadates, oxides, glasses, etc. Suitable matrices are known e.g. from WO 2006/024530 A1.

Example 3

Luminescence System 1: Er,Yb:Matrix, Tm:YIG
Luminescence System 2: Yb,Ho:Matrix, Mixed with Ho:YIG The employment of mixtures of luminophores as luminescence systems is advantageous in particular when the different luminescence systems (luminescence system 1 and luminescence system 2) are integrated into the value document mutually independently, e.g. metered with different control loops or from different metering stations, or are integrated into the ink mutually independently with different quality assurance systems.

For the two luminescence systems then vary (e.g. the intensities of the lines belonging to the two luminescence systems). From place to place on the bank note or from bank note to bank note of a BN series (or of a production lot) the two luminescence systems, and in particular their intensities, are thus mutually independent and vary mutually independently.

If the luminophores in the luminescence systems 1 and 2 are assigned defined intensities, i.e.
Luminescence system 1: I11, I12
Luminescence system 2: I21, I22
for the respective luminophores L11, L12, L21, L22 of the systems, additional security is obtained in the overall system (consisting of luminescence system 1 and luminescence system 2), because the intensity ratio I21/I22 (and/or I11/I12) adjusted via the powder mixture of the luminescence system 2 is revealed only when excitation is done at the "right" wavelength for the luminescence system 1 or luminescence system 2.

These relations thus remain reserved only for the defining authority, e.g. a central bank, and could be employed for authenticating the bank note.

If excitation is done at a wavelength at which the two luminescence systems are jointly excitable, i.e. the luminescence system 1 responds to the excitation with I11 and the luminescence system 2 with I21, there is obtained for the joint line for example a mixture of (I11+I21), which need not have a defined connection with the intensities I12 and I22, because the two luminescence systems have defined intensity ratios only in relation to themselves, but no joint basis for intensity due to their generally independent metering.

The two luminescence systems 1 and 2 can alternatively have a defined mutual relation. Then the two intensity pairs I11, I12 and I21, I22 are moreover also interlaced.

Besides the interrelation of the intensities, further properties of the luminescence systems can be measured and put in mutual relation for authentication.

Special embodiments in the method for authenticating the value document can be obtained in different ways.

Characteristic luminescence times. Measurement of a joint luminescence time characteristic of the value document, upon excitation at a wavelength which excites both systems. Measurement of different luminescence times characteristic of the individual systems, luminescence system 1 and luminescence system 2, upon excitation into the respective subsystem. The characteristic luminescence times can be rise times as well as decay times, whereby the durations of illumination can differ and can be adapted to the respective subsystem, or also be identical. Likewise, illumination times differing over the bank note can be employed, whereby the decay times of the joint emission can be put in relation to decay times of other transitions for the determination of authentication.

Intensity ratios. Measurement of the total intensity of the two luminescence systems. Measurement of the individual intensities of the two luminescence systems by measurement upon the possibly joint excitation, and putting in relation to the intensities of the partial systems (upon excitation by means of the one or the several individual excitations). Putting all these luminescence intensities in mutual relation for authenticating the paper of value.

Spectral properties. Upon joint excitation the joint emission shows the superimposition of the spectra of the two luminescence systems. The spectrum is changed, e.g. broadened, shifted, changed in shape, relative to that of the luminescence system 1 as well as relative to that of the luminescence system 2. Upon different excitation or excitability there is obtained a different spectral shape. The spectral shapes of individual/separate/joint excitation can also be put in mutual relation for authentication.

The stated differences can also be employed for forming encodings, i.e. for mutually distinguishing different value documents that are constructed according to the same system, e.g. denominations, series, etc.

The luminescence systems can be incorporated into a value document in different ways.

An embedding into the value document can be effected into the substrate (paper and/or plastic), the printing ink, into authentication features (security thread, fibers, planchets, etc.).

The incorporation of the two luminescence systems L1 and L2 can be effected by means of separate quality assurance systems with independent metering stations. However, the incorporation of the two luminescence systems L1 and L2 can also be effected by means of coupled quality assurance systems or a single metering station, so that the two systems (and, by derivation, the intensities arising upon the metering) have a defined connection. This connection can characterize the production lot, the series, or other information.

A checking method for verifying the presence of a security element having at least two luminescent substances or two luminescence systems can be effected by means of a sensor or several sensors. The sensor or sensors evaluate the individual luminescence systems, e.g. by putting the possibly multiple intensities of the individual luminescence systems in a relation. Likewise by exciting via different wavelengths l1 (jointly excitable) and/or l2 (only system 1) and/or l3 (only system 2). Optionally or additionally by irradiating the wavelengths l1, l2 and l3 alternatingly and/or jointly. Further, it is possible to excite in spatially different fashion, e.g. one measuring track with l1, another measuring track with l2. Upon evaluation, all conceivable properties, e.g. luminescence times, intensity ratios, spectral properties, etc., can be taken into consideration, e.g. for authenticating a value document.

Figure 2A:
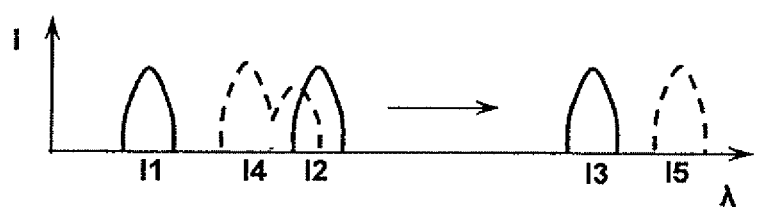
FIGS. 2a-2b show excitation bands and emission bands of further security elements.
Figure 2B:
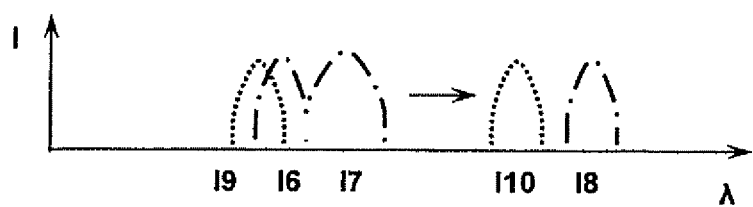

In FIG. 2a there are represented intensities as a function of wavelength for a first luminescence system 1. In FIG. 2b there are represented intensities as a function of wavelength for a second luminescence system 2.

Luminescence system 1 consists of two luminophores. A first luminophore represented with continuous lines absorbs at l1 and l2 and emits at l3 and possibly further wavelengths not represented. A second luminophore represented with dashed lines absorbs for example at l4 and l2 and emits at l5.

Luminescence system 2 likewise consists of two luminophores. A third luminophore represented with dot-dashed lines absorbs at l6 and l7 and emits at l8 and possibly further wavelengths not represented. A fourth luminophore represented with dotted lines absorbs at l9, in the example equal to l6, and emits at l10.

If excitation is done with a wavelength l2, approximately equal to l7, luminescence system 1 thus emits at l3 (and l5) as well as luminescence system 2 (at l8). The emissions at l3 and l8 overlap with each other, i.e. cannot be mutually discriminated in a sensor. Accordingly there is obtained a superimposed spectrum of a continuous and dot-dashed curve, which curve is different from the single lines spectrally as well as with respect to its characteristic shape, luminescence times, intensities.

If excitation is done with a wavelength l6, there is obtained from the overlapping bands l3, l8 only the band l8 (together with the characteristic physics) of the luminescence system 2. If excitation is done with a wavelength l1, there is obtained only the band l3 (together with the characteristic physics) of the luminescence system 1. This shows that it is not always necessary to excite a total luminescence system (here 1 and 2) with a wavelength.

The two luminescence systems (1 and 2) can now be adjusted such that the spectral shape, intensities, decay times, etc., of the luminescence system 1 (i.e. dashed and continuous curves) as well as those of the luminescence system 2 (dotted and dot-dashed curves) are interrelated. This means that for authentication, i.e. e.g. recognition as a valid value document, there are one or several laws that must be obeyed in the parameters.

A forger is hence faced with the problem of not knowing at which wavelengths the corresponding values have been put in mutual relation. This considerably increases the safeguarding of authenticity. This holds in particular when the two luminescence systems 1 and 2 are brought into or onto the value document mutually independently. Alternatively also when they are incorporated or applied jointly, but the values are deliberately varied. Alternatively, the relation can also be kept constant and the sums of the intensities then also be quantitatively evaluated.

Hereinafter the construction of sensors will be described. They can be employed in an automatic checking machine in which value documents to be checked are moved past the sensors, as well as in a hand-held unit.

Employment of two independent sensors that are not interrelated. Each sensor measures for itself its own luminescence system. For this purpose, it excites at least at the wavelengths (and detects at the wavelengths) that isolate its own luminescence system. Particularly preferably, at least one of the sensors moreover also detects with an excitation that excites both luminescence systems and uses this information for authentication of the value document, e.g. by the intensity ratio being formed by its own line and the joint line, whereby the intensity ratio is put in relation to the known, expected intensity ratio of the individual or both luminescence systems. There can be exploited all physical characteristics, in particular luminescence times, intensities, spectra, spectral shapes, etc.

Employment of an independent sensor and a combination sensor. The independent sensor measures exclusively its luminescence system (like independent sensors). In so doing, the sensor can ascertain the second system, but it evaluates no further information about the second system. In the combination sensor has been or is stored or procured, e.g. from statistical evaluations, information about both luminescence systems. This information is employed for authenticating the value document. There can be exploited all physical characteristics, in particular luminescence times, intensities, spectra, spectral shapes, etc.

Employment of a multisensor. There is employed only one sensor which can (but does not have to) measure all described properties of both luminescence systems. That is, the sensor excites and evaluates the two luminescence systems separately or jointly. There can be exploited all physical characteristics, in particular luminescence times, intensities, spectra, spectral shapes, etc.

Not only the joint emission can be detected. Furthermore, additional emission lines and/or excitation lines of the luminescence systems can also be detected to increase security.

Hereinafter several authentications will be described. The authentications are realized in sensors. It is particularly preferable when sensors differ e.g. in different processing steps in an authentication level or over authentication levels. For then it is more difficult for the forger to analyze the mode of operation of the sensor. Preferably, several of these authentications are integrated in a sensor. This is advantageous in particular because different authentications (here e.g. intensities) can be put in mutual relation to arrive at the authentication result. By "relation" it is to be understood here that intensity bands, intensity ratios, intensity thresholds, regions, positive and negative detections (with thresholds) and others are compared. The following Table 2 contains a generalized representation of the above example.

Example of Reading (Authentication 1):

Luminescence system LS1 consists of the luminophores LS11 and LS12. Luminescence system LS2 consists of the luminophores LS21 and LS22.

For luminescence system LS1 it holds: Luminophore LS11 is excitable at the excitation wavelengths 1 and 2 (and possibly also at others). The term "wavelengths" or "excitation wavelengths" is to be understood here as "excitation bands". Luminophore LS12 is excitable at the excitation bands 3 and 4 (and possibly also at others). When luminophore LS11 is excited, it shows the emission bands A and b (and possibly also others). When luminophore LS12 is excited, it shows the emission bands c and d (and possibly also others). The same holds for luminescence system LS2.

Upon authentication 1 irradiation is done into the band 1 of LS1 ("x") in which LS2 possesses no excitation (therefore 2x "n.a."). When irradiation is done into the band 1 of LS1, the latter emits with the emission band A ("e" in the table). LS21 is not excited at this wavelength according to the invention, however, and therefore shows no emission (in particular not at emission band A).

Simultaneous excitation of LS12: optionally the excitation in band 1 of LS11 can also excite LS12 (in its band 3). Then LS12 also emits with its bands c and d.

Simultaneous excitation of LS22: optionally the excitation in band 1 of LS11 can also excite LS22 (in its band 7). Then LS22 also emits with its bands g and h.

Temporally shifted or spatially shifted excitation of L12 or L22 with 2nd excitation wavelength: optionally the authentication can also be effected by means of a further wavelength that excites LS12 at band 3 and/or LS22 at band 7, but not LS21. This would be the case of a temporally alternating and/or spatially shifted 2nd excitation. That is to say, band 3 of LS12 can, but does not have to, lie at the same wavelength as band 1 of LS11.

TABLE 2

| | | Excitations | | | | | | | | Luminescence system | Emissions | | | | | | | |
| --- | --- | --- | --- | --- | --- | --- | --- | --- | --- | --- | --- | --- | --- | --- | --- | --- | --- | --- |
| | | LS1 | | | | LS2 | | | | | LS1 | | | | LS2 | | | |
| | | LS11 | | LS12 | | LS21 | | LS22 | | Luminophore | LS11 | | LS12 | | LS21 | | LS22 | |
| Name | Detection | 1 | 2 | 3 | 4 | 5 | 6 | 7 | 8 | Wavelength/Band | A | b | c | d | A | f | g | h |
| Authentication 1 | selectively LS11 | x | | opt | | na | na | opt | | | e | opt | opt | opt | / | / | opt | opt |
| Authentication 2 | jointly LS11/LS21 | | x | opt | | x | | opt | | | e | opt | opt | opt | e | opt | opt | opt |
| Authentication 3 | selectively LS21 | na | na | opt | | x | | opt | | | / | / | opt | opt | e | opt | opt | opt |
| Authentication 4 | selectively LS12 | | opt | x | | | opt | | opt | | opt | opt | e | opt | opt | opt | opt | opt |
| Authentication 5 | selectively LS22 | | opt | | opt | | opt | x | | | opt | opt | opt | opt | opt | opt | e | opt |
| Authentication 6 | LS1 completely | x | add | x | add | / | / | | opt | | e | opt | e | opt | / | / | opt | opt |
| Authentication 7 | LS2 completely | / | / | opt | | x | add | x | add | | / | / | opt | opt | e | opt | opt | opt |
| Authentication 8 | LS1 and LS2 completely | x-1 | opt | x | opt | x-2 | opt | x | opt | | e-1 | opt | e | opt | e-2 | opt | e | opt |

The symbols mean:
x is excitable there
opt. is optionally excitable
n.a. is not excitable
/ shows no emission
e is detected there
add. temporally/spatially separate additional excitation
x-1, x-2 temporally or spatially separate
e-1 emission upon excitation of x-1
e-2 emission upon excitation of x-2

Example 4

Feature system consisting of luminescence system 1 and luminescence system 2:

Luminescence system 1: LS11: Er:La2O2S, LS12: Mn:Li3PO4

Luminescence system 2: LS21: Nd,Yb:Y2O2S, LS22: Yb,Tm:YVO4

The concentration of Tm is chosen so small in Yb, Tm here that it possesses no substantial excitation in the visible and near infrared, i.e. possesses less than 10% of the excitation intensity of the systems LS11 and LS21 in the excitation spectrum at 1 µm. The feature system is integrated into the value document by luminescence system 1 and luminescence system 2 being incorporated into the volume of the value document mutually independently (but simultaneously). For this purpose, the features are e.g. dispersed and the dispersions added to the pulp homogeneously during papermaking. Both luminescence systems are monitored by suitable, mutually independent quality control devices, so that their target intensities conform to the specifications.

For authentication of the value document there are sensors available which are integrated e.g. into bank-note processing machines. The sensors can also be designed as hand-held units, etc., independently of bank-note processing machines Authentication 1 (for LS11)

Excitation at 650 nm (since LS11 is excitable here, but not LS21) and detection of LS11 at a wavelength of approx. 1 µm. Optionally the sensor additionally detects LS11 at a wavelength of 1.5 µm and puts this intensity in mutual relation to the intensity at approx. 1 µm. Optionally the sensor detects Mn:Li3PO4 at its emission wavelength and puts this intensity in mutual relation to the intensity at approx. 1 µm.

Authentication 2 (Combination of LS11 and LS21)

Excitation at 520 nm (since LS11 as well as LS21 are excitable here) and detection of a combination of LS11 and LS21 at a wavelength of approx. 1 µm. Optionally detection of LS11 additionally at a wavelength of 1.5 µm and puts this intensity in mutual relation to another measured intensity of LS1 and/or LS2 (or a combination of the two).

Authentication 3 (for LS21)

Excitation at 584 nm (since LS21 is excitable here, but not LS12) and detection of LS21 at a wavelength of approx. 1 µm.

Authentication 7 (for LS21 and LS22)

Excitation at 580 nm (since LS21 is excitable here, while LS11 is not excitable) and detection of LS21 at a wavelength of approx. 1 µm. Excitation can be shifted temporally or spatially at approx. 0.95 µm (since LS22 is excitable here) and detection of LS22 at a wavelength of approx. 1.8 µm. The intensities are put in mutual relation.

Authentication 6 (for LS11 and LS12)

Excitation at 660 nm (since LS11 and LS12 are excitable here, but LS21 shows no excitation) and detection of LS11 at a wavelength of approx. 1 µm. Optionally LS11 additionally at a wavelength of 1.5 µm. LS12 at a wavelength of approx. 1.2 µm. The intensities are put in mutual relation and are checked for example for the known intensity ratios.

Authentication 8 (for LS1 and opt. LS2)

Excitation at approx. 1 µm (since all systems are excitable here) and detection. Mixture of LS11, LS21, LS22 at a wavelength of approx. 1 µm. LS11 at a wavelength of approx. 1.5 µm. LS12 at a wavelength of approx. 1.2 µm. LS22 at a wavelength of approx. 1.8 µm. The intensities are put in mutual relation and checked for example for the known intensity ratios.

Optionally, all authentications alternatively or additionally measure characteristic luminescence times and/or spectra by spectral analysis or shape analysis of the spectrum. That is, instead of the intensity, the characteristic luminescence time, spectral shape, etc., could also be checked as an authentication criterion.

In a preferred embodiment, there are used for authentication two mutually independent sensors which carry out the authentications 6 and 7. In this way the two luminescence systems 1 and 2 are operated mutually independently, but they overlap in a joint line to make it decisively more difficult for the forger to recognize the intrasystem connections. The sensors rate the two luminescence systems mutually independently according to the invention. Optionally, they moreover rate at least also the existence of the second luminescence system.

In a further preferred embodiment, the authentications 1 and 2 are carried out. In this way luminescence system 1 is detected independently and the sensor belonging to the luminescence system 2 performs a rating of luminescence system 2 such that it takes into consideration for the sensed data its system-inherent knowledge of luminescence system 2 that is known only to it.

In a particularly preferred embodiment, there is at least e.g. in the central bank a master sensor which combines the authentications 6, 7 in one sensor. It can thus exploit for authentication not only the relations of each individual luminescence system, but moreover check a known relation [or the presence of no defined relation] between the systems. In a particularly preferred embodiment, there is used for this purpose a sensor that illuminates with several excitation sources (wavelengths) and captures the response of the feature system spectroscopically in many channels. The spectroscopic solution can be solved here via a spectrometer, tunable filters, graduated filters, several discrete filter channels or combinations thereof.

The authentication of the bank note can be effected in multi-step fashion here, as described above.

The described security element can be employed for verifying the authenticity of the objects having the security element. The security element can, however, represent an encoding instead or additionally. In bank notes the encoding can identify for example the currency and/or the denomination of the bank notes. Likewise, the encoding can contain a statement about the series of the bank notes.

The invention claimed is:

1. A security element comprising:
a first luminescent substance having a first emission spectrum, the first emission spectrum including one or more emission bands; and
a second luminescent substance having a second emission spectrum, the second emission spectrum including one or more emission bands, wherein
the one or more emission bands of the first emission spectrum include an emission band that overlaps an emission band of the second emission spectrum to form a joint emission band,
the first and the second luminescent substances each have a first excitation band that produces an emission at the joint emission band,
the first excitation band of the first luminescent substance and the first excitation band of the second luminescent substance overlap at a joint excitation band, and
the first luminescent substance further has a second excitation band that produces an emission at the joint emission band,
the second excitation band of the first luminescent substance is distinct from the first excitation band of the first luminescent substance, and
the second excitation band of the first luminescent substance is distinct from the first excitation band of the second luminescent substance.

2. The security element according to claim 1, wherein first and second luminescent substances have a complete or partial spatial overlap.

3. The security element according to claim 1, wherein the security element comprises additional luminescent substances.

4. A value document comprising the security element recited in claim 1, wherein the value document comprises at least one of paper and plastic.

5. The value document according to claim 4, wherein the security element is at least one of incorporated into the volume of the value document and applied to the value document.

6. The value document according to claim 4, wherein the security element is applied to the value document as an invisible, at least partial coating.

7. The value document according to claim 4, wherein the security element is admixed to a printing ink on the value document.

8. The value document according to claim 4, wherein the first luminescent substance and the second luminescent substance are combined with at least one other authentication feature.

9. An authentication feature for a value document that includes a carrier material, comprising at least one security element as recited in claim 1, wherein the security element is one or both of embedded in the carrier material and applied to the carrier material.

10. The authentication feature according to claim 9, wherein the authentication feature has the form of a strip, a band or a liquid.

11. The authentication feature according to claim 9, wherein the carrier material is configured as a security thread, planchet, mottling fiber, label or ink.

12. A method for manufacturing the value document recited in claim 4, the method comprising adding the security element to a printing ink, and printing the value document.

13. A method for manufacturing the value document recited in claim 4, the method comprising applying the security element by a coating process.

14. A method for manufacturing the value document recited in claim 4, the method comprising incorporating the security element into the volume of the value document.

15. A checking method for verifying the presence of the security element of claim 1, the method comprising:
illuminating the luminescent substances with a first radiation which has a wavelength lying substantially at the first excitation band of the first or of the second luminescent substance that causes an emission at the joint emission band only of the first luminescent substance or the second luminescent substance.

16. The checking method according to claim 15, including recognizing the presence of the security element if an emission occurs at the joint emission band upon excitation with the first radiation.

17. The checking method according to claim 15, including, for exciting the luminescent substances, employing a second radiation which lies at one of the excitation bands of the first or second luminescent substance which is not excited by the first radiation.

18. A method for manufacturing the authentication feature according to claim 9, the method comprising
applying the security element by a coating process or adding the security element to a printing ink, and
printing the value document or the authentication feature with said ink.

19. A method for manufacturing the authentication feature recited in claim 11, the method comprising incorporating the security element into the volume of the authentication feature.

20. The security element according to claim 1, wherein the first luminescent substance comprises a single luminophore and the second luminescent substance comprises a mixture including at least two luminophores.

21. The security element according to claim 1, wherein the second luminescent substance is not excitable at the first excitation band of the first luminescent substance.

22. The security element according to claim 1, wherein the first excitation band of the first luminescent substance does not overlap with the joint excitation band.

23. A checking method for verifying the presence of the security element recited in claim 1, the method comprising the steps:
illuminating the luminescent substances with a first radiation which has a wavelength lying substantially at the first excitation band of the first luminescent substance;
detecting the emission at the substantially identical joint emission band;
illuminating the luminescent substances with a second radiation which has a wavelength lying substantially at the first excitation band of the second luminescent substance; and
detecting the emission at the substantially identical joint emission band.

24. The security element according to claim 1, wherein the first emission band of each of the first and the second luminescent substances cannot be mutually discriminated using sensors with a resolution of less than 10 nm.

25. The security element according to claim 1, wherein the first emission band of each of the first and the second luminescent substances cannot be mutually discriminated using sensors with a resolution of less than 50 nm.

26. The security element according to claim 1, wherein the second excitation band of the first luminescent substance does not overlap the first excitation band of the first luminescent substance, or
the second excitation band of the first luminescent substance does not overlap the first excitation band of the second luminescent substance.

27. The security element according to claim 1, wherein the first excitation band of the first luminescent substance, the second excitation band of the first luminescent substance, and the first excitation band of the second luminescent substance each have a peak, and
the peak of the second excitation band of the first luminescent substance is distinct from the peak of the first excitation band of the first luminescent substance, or
the peak of the second excitation band of the first luminescent substance is distinct from the peak of first excitation band of the second luminescent substance.

* * * * *